(12) United States Patent
Tanimoto et al.

(10) Patent No.: US 7,884,235 B2
(45) Date of Patent: Feb. 8, 2011

(54) METHOD FOR GAS-PHASE CATALYTIC OXIDATION USING A FIXED BED REACTOR

(75) Inventors: Michio Tanimoto, Himeji (JP); Shin-yuki Masaki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 11/826,629

(22) Filed: Jul. 17, 2007

(65) Prior Publication Data
US 2008/0021240 A1 Jan. 24, 2008

(30) Foreign Application Priority Data

Jul. 20, 2006 (JP) ............................. 2006-198722
Mar. 9, 2007 (JP) ............................. 2007-060460

(51) Int. Cl.
*C07C 53/00* (2006.01)

(52) U.S. Cl. ..................... 562/512; 562/512.2; 562/545

(58) Field of Classification Search .............. 562/512.2, 562/545
See application file for complete search history.

(56) References Cited

U.S. PATENT DOCUMENTS

| | | | |
|---|---|---|---|
| 5,442,108 A | 8/1995 | Kawajiri et al. | |
| 6,069,271 A | 5/2000 | Tanimoto et al. | |
| 7,238,817 B1 * | 7/2007 | Han | 549/538 |
| 2003/0006026 A1 * | 1/2003 | Matsumoto et al. | 165/157 |
| 2006/0235243 A1 | 10/2006 | Fukumoto | |

FOREIGN PATENT DOCUMENTS

| | | |
|---|---|---|
| EP | 1 270 065 | 1/2003 |
| GB | 2 063 861 | 6/1981 |
| JP | 6-262081 | 9/1994 |
| JP | 6-263689 | 9/1994 |
| JP | 11-130722 | 5/1999 |
| JP | 2006-298797 | 11/2006 |

* cited by examiner

*Primary Examiner*—Sudhakar Katakam
(74) *Attorney, Agent, or Firm*—Wenderoth, Lind & Ponack, L.L.P.

(57) ABSTRACT

The invention provides a method of gas-phase catalytic oxidation, in particular, a production method of (meth)acrylic acid, which enables stable continuous operation of gas-phase catalytic oxidation over a long term, maintaining high yield and suppressing increase in pressure loss. In the method a fixed bed reactor is used, in which a treating agent for removing organic substance and/or carbides, preferably a treating agent having an adsorption capacity of at least 0.05% by mass, as measured by crotonaldehyde as an indicator of organic substance, is disposed on the upstream side of the gas-phase oxidation catalyst layer in respect of the direction of the gas flow. It is desirable that at least a part of the treating agent is exchanged at a frequency of at least once a year.

5 Claims, No Drawings

METHOD FOR GAS-PHASE CATALYTIC OXIDATION USING A FIXED BED REACTOR

This invention relates to an improvement in a method for gas-phase catalytic oxidation using a fixed bed reactor.

BACKGROUND ART

In the field of petrochemical industry, gas-phase catalytic oxidation reaction using a fixed bed reactor is frequently practiced. Whereas, starting materials used in these gas-phase catalytic oxidation reactions do not necessarily have high purity.

For example, in the production of acrylic acid or methacrylic acid (hereafter collectively referred to as "(meth) acrylic acid"), first hydrocarbons are converted into unsaturated aldehydes in the first stage gas-phase catalytic oxidation step, and then in the second stage gas-phase catalytic oxidation step, the unsaturated aldehydes are converted into (meth) acrylic acid. In these reactions, normally the unsaturated aldehydes are not isolated and purified in midway the process, but the reaction gas produced in the first stage gas-phase catalytic oxidation step is introduced into the second stage gas-phase catalytic oxidation step either as it is, or after addition of molecular oxygen where necessary, to provide (meth)acrylic acid. Consequently, due to deposition and accumulation of organic substance or carbides generated from impurities contained in the starting materials of the reaction (hereafter these are collectively referred to as "catalyst inhibitor") on the gas-phase catalytic oxidation catalyst in the first stage ("the first stage catalyst"), or due to deposition and accumulation of catalyst inhibitor generated from by-products and the like formed of the first stage reaction on the gas-phase catalytic oxidation catalyst in the second stage ("the second stage catalyst"), when these catalysts are used in the reactions continuously over a fixed period, such problems are caused as, for example, drop in the yield of the object product with time, resulting from deterioration in catalyst's performance and increase in the pressure loss at the catalyst layers.

As methods for solving such problems, for example, JP Hei 6(1994)-262081A and JP Hei 6(1994)-263689A (corres. to U.S. Pat. No. 5,442,108) disclose a method of regenerating the catalyst by regularly treating, e.g., burning, the catalyst inhibitor. More specifically, the prior art references disclose methods of safely and efficiently regenerating the catalyst by regularly suspending the reaction and heat-treating the catalyst as retaining its state of being filled in the reaction tube(s), while passing a gaseous mixture containing molecular oxygen and steam through the reaction tube(s). These methods have a merit of enabling regeneration of the catalyst, without taking it out from the reaction tube(s). However, because of the thermal load exerted on the catalyst during the high temperature treatment, the catalyst life may be shortened by every regeneration treatment depending on the kind of the catalyst. The methods that induce reduction in the catalyst life cannot be an economically satisfactory solution, and a method which enables stable continuous operation over a prolonged period is in demand.

Problem to be Solved by the Invention

Accordingly, therefore, the object of the present invention is to provide a method for gas-phase catalytic oxidation, in particular, production method of (meth)acrylic acid by gas-phase catalytic oxidation, which enables stable continuous operation over a prolonged period while maintaining high yield level and suppressing increase in the pressure loss.

Means for Solving the Problem

We have engaged in concentrative studies with the view to accomplish the above object, and discovered: in conducting gas-phase catalytic oxidation with a fixed bed reactor having reaction tube(s) filled with gas-phase oxidation catalyst, when a treating agent for removing the catalyst inhibitor in the reaction gas, the treating agent preferably having an adsorption capacity of at least 0.05% by mass, as measured by crotonaldehyde as an indicator of organic substance, is disposed on the upstream side of the catalyst layer, preferably regularly exchanging at least a part of the treating agent, catalyst deterioration can be prevented and stable continuous operation over a prolonged period maintaining high yield and suppressing increase in the pressure loss at the catalyst layer(s) becomes possible.

Thus, according to the present invention, a method of gas-phase catalytic oxidation is provided, in which the gas-phase catalytic oxidation is continuously operated, the method being characterized by using a fixed bed reactor in which a treating agent for removing the catalyst inhibitor in the reaction gas is disposed on the upstream side of the gas-phase oxidation catalyst layer in respect of the direction of the gas flow, preferably the treating agent having an adsorption capacity of at least 0.05% by mass, as measured by crotonaldehyde as an indicator of organic substance, and preferably at least a part of the treating agent being exchanged at a frequency of at least once a year. In the gas-phase catalytic oxidation method of the present invention, preferably the treating agent is disposed in the reaction tube(s) and/or in a space within the reactor, for example, on the upper part of a tube-holding upper plate in the reactor.

Removal of the catalyst inhibitor as referred to herein signifies to effectively adsorb, absorb or deposit the organic substance or carbides formed, which are attributable to impurities contained in the starting materials for the reaction or by-products produced in the first stage reaction, onto the treating agent to eliminate them from the reaction gas and prevent any contact between the catalyst inhibitor and the catalyst.

In the method for gas-phase catalytic oxidation of the present invention, preferably a regenerated treating agent is used as at least a part of the treating agent, which leads to reduction in the production costs.

This invention is conveniently used for producing (meth) acrylic acid by two-stage gas-phase catalytic oxidation of such starting materials as propylene, isobutylene, t-butyl alcohol, methyl-t-butyl ether and the like with molecular oxygen, in the presence of a catalyst. In particular, the method is most conveniently used for the production of acrylic acid by two-stage oxidation of propylene, using a tandem type reactor.

Effect of the Invention

The method for gas-phase catalytic oxidation of the present invention can suppress deposition of the catalyst inhibitor onto the catalyst and enables to conduct stable gas-phase catalytic oxidation continuously over a prolonged period without deterioration of the catalyst itself, maintaining high yield and suppressing the increase in the pressure loss at the catalyst layers. Therefore, according to the production method of the present invention, drastic reduction in the production cost of (meth)acrylic acid can be expected.

BEST EMBODIMENT FOR WORKING THE INVENTION

The method for gas-phase catalytic oxidation of the present invention comprises using a fixed bed reactor having a reaction tube or tubes filled with a gas-phase oxidation catalyst (which hereafter may be referred to simply as "catalyst"), disposing a treating agent for removing the catalyst inhibitor, preferably a treating agent having an adsorption capacity of at least 0.05% by mass, as measured by crotonaldehyde as an indicator of organic substance, in the flowing path of the gas containing the starting material and/or the produced compound (the disposition site may be hereafter referred to simply as "in the reactor"), and preferably exchanging at least a part of the treating agent at a frequency of at least once a year.

Here the "fixed bed reactor" means an apparatus in which, in the presence of a gas-phase oxidation catalyst statically filled in its reaction tube(s), a starting gas fed through the gas inlet(s) of the reaction tube(s) is subjected to gas-phase catalytic oxidation and the gas containing the final product is discharged through the gas outlet(s) of the reaction tube(s). It may be a stand-alone apparatus or may be one which is incorporated into a production plant.

The fixed bed reactor useful in the present invention has substantially the same structure as that of generally used fixed bed reactors for gas-phase catalytic oxidation, except that a treating agent for removing catalyst inhibitor is disposed in the reactor, and is subject to no particular limitation. Therefore, the fixed bed reactor of the present invention can be, for example, a shell-and-tube reactor in which a catalyst is filled in many small-diameter reaction tubes, or an insulated reactor in which a catalyst is filled in single large-diameter reaction tube.

According to the invention, the treating agent is preferably exchanged at least once a year, more preferably at least twice a year. When the treating agent is continuously used over a long term without the exchange, elimination of the catalyst inhibitor becomes incomplete, which allows deposition of the catalyst inhibitor on also the catalyst layer(s), leading to such inconveniences as reduction in the catalytic activity or increase in the pressure loss. The amount of the treating agent to be exchanged per one exchange can be suitably selected depending on the used conditions, and a part or the entire amount of the treating agent can be exchanged.

As the exchanging means, any known method of exchange can be adopted. For example, the treating agent can be sucked from an upper part of the reaction tube(s) using a suction pipe, as described in JP 2002-301355A or, as in International Publication WO 98/02239, the treating agent can be sucked while introducing a pressurized gas into the reaction tube(s). In the occasion of exchanging the treating agent, a new or reclaimed agent can be used.

Here the "reclaimed agent" means once used treating agent from which, after having been withdrawn from the reaction tube(s), the catalyst inhibitor deposited thereon is removed by heat treatment or washing. Conditions of the heat treatment or washing are not particularly limited but can be suitably determined according to the deposited amount of the catalyst inhibitor.

As the heat treating conditions, such an atmosphere, temperature and time as will enable elimination of the catalyst inhibitor deposited on the treating agent by combustion and will not degenerate the treating agent should be selected. Usually it is sufficient to conduct it in an atmosphere of a molecular oxygen-containing gas, at 300-700° C. for 2-72 hours, preferably in air at 350-600° C. for 3-24 hours.

The washing can be conducted under such conditions as will enable elimination of the catalyst inhibitor deposited on the treating agent and will not degenerate the treating agent. Washing with, for example, an acid, alkaline aqueous solution or organic solvent can be conducted. The washing effect can be improved when heating is concurrently conducted.

The treating agent used in the present invention is subject to no particular limitation, so long as it is capable of eliminating the organic substance or carbides generated from the impurities contained in the starting material of the reaction or the by-products produced of the first stage reaction. Examples of useful treating agent include oxide, complex oxides or carbonates (hereafter collectively referred to as "(complex)oxides and the like"), which contain at least one element selected from aluminum (Al) silicon (Si), titanium (Ti), zirconium (Zr), zinc (Zn), magnesium (Mg), calcium (Ca) and niobium (Nb) or their mixtures. As specific examples, alumina, silica, titania, zirconia, silica-alumina, silica-titania, silica-zinc oxide, silica-zirconia, alumina-titania, alumina-zinc oxide, alumina-zirconia, titania-zirconia, zinc oxide-zirconia, zeolite, magnesium carbonate, calcium carbonate and the like can be named. Of those treating agents, oxides or complex oxides containing at least one element selected from aluminum, silicon, titanium and zirconium, in particular, complex oxides containing aluminum and silicon, are preferred.

The treating agent which is a complex oxide containing aluminum and silicon can be prepared, for example, by shaping a mixture of alumina powder with colloidal silica into a desired form and calcining it. In that case, per 100 mass parts (in terms of oxide) of the total amount of the alumina powder and colloidal silica, the amount of the alumina powder is 30-97 mass parts, preferably 40-95 mass parts, inter alia, 50-90 mass parts; and that of the colloidal silica is 3-70 mass parts, preferably 5-60 mass parts, inter alia, no more than 50 mass parts. Preferred calcination temperature ranges 500° C.-1300° C., more preferably 600° C.-1200° C., inter alia, 700° C.-1100° C. Preferred calcination time ranges 0.5-50 hours, in particular, 1-20 hours.

The treating agent which is a complex oxide containing aluminum and silicon can also be prepared by, for example, shaping a mixture of alumina powder, alumina sol and colloidal silica into a desired form and calcining it. In this case, per 100 mass parts of the total amount of the alumina powder, alumina sol and colloidal silica, the sum of the alumina powder and alumina sol is 60-97 mass parts, preferably 70-95 mass parts, inter alia, 80-90 mass parts; and the colloidal silica blended is 3-40 mass parts, preferably 5-30 mass parts, inter alia, 10-20 mass parts.

Also per 100 mass parts of the total amount of the alumina powder and alumina sol, the blended amount of the alumina powder is 60-97 mass parts, preferably 70-96 mass parts, inter alia, 85-95 mass parts; and that of the alumina sol is 3-40 mass parts, preferably 4-30 mass parts, inter alia, 5-15 mass parts.

Preferred calcination temperature ranges 600° C.-1300° C., more preferably 650° C.-1200° C., inter alia, 700-1100° C. Preferred calcination time ranges 0.5-50 hours, in particular, 1-20 hours.

The treating agent may also take a form of a mixture containing two or more of above (complex)oxides and the like, or a (complex)oxide and the like as carried on another (complex)oxide and the like, or a mixture of above (complex) oxide and the like with a solid other than the above-named, or a (complex)oxide and the like as carried on a solid other than the above-named.

Shape of the treating agent is not critical, but any optional shape may be chosen. For example, those shaped with ordinary tabletting machine, extrusion molding machine or granulating machine, such as sphere, column, cylinder, star, ring, tablet, pellet and the like can be named. Where the treating agent has too small a size, it causes increase in the pressure loss to hamper effective reaction. Conversely, when its size is too large, insufficient catalyst inhibitor elimination may result. Hence, its preferred average diameter should be within a range of 1 mm-15 mm, more preferably 2 mm-12 mm, inter alia, 3 mm-10 mm. Also two or more of the treating agents of different sizes can be used as packed into plural layers, or plural treating agents of different sizes may be used as mixed, so long as their sizes fall within the above-specified range of average diameter.

The adsorption capacity of treating agent using crotonaldehyde as an indicator of organic substance can be measured as follows. Whereas, similar measurement method may also be used so long as it allows measurement of substantial adsorption capacity of the treating agent. A prescribed amount of a treating agent is filled in a temperature-controllable fixed bed flow device and maintained at 350° C. under flowing nitrogen or air. Crotonaldehyde is gasified with vapor pressure in a bubbling device or the like, or adjusted of the amounts of its vapor and evaporation to attain a prescribed concentration using an evaporator or the like, by controlling the temperature or feed rate, and introduced from the upstream side of the treating agent. After passing the gaseous crotonaldehyde for a prescribed period, the treating agent is withdrawn, heat-treated at a high temperature. Either by measuring its mass change before and after the treatment or measuring the mass change with thermal analyzer, the organic matter adsorption can be determined.

Use rate of the treating agent may be suitably adjusted according to the kind, specific gravity and shape of individual treating agent used, and the kind, specific gravity, shape and use rate of the catalyst, and is not subject to any particular limitation. Whereas, when it is too low, elimination of the catalyst inhibitor may not be sufficiently achieved. Conversely, when it is too high, more than the necessary amount of the treating agent is used to lead to rise in the production cost. Hence, the use rate of the treating agent in terms of the treating agent: catalyst (volumetric ratio) is preferably 1:05-100, more preferably 1:2-50, inter alia, 1:3-30.

In a fixed bed reactor used in the present invention, the place of disposing the treating agent in the reactor can be one which is adequate to suppress deposition of the catalyst inhibitor onto the catalyst used, and is not particularly limited so long as the treating agent alone can be withdrawn and refilled. Preferably, when it is disposed at a place whereat the gas temperature is lower than that at the catalyst layer(s), i.e., than the reaction temperature, its elimination effect of the catalyst inhibitor is enhanced. It is, therefore, advantageous to dispose the treating agent at the upper side of the reaction tube(s), more specifically, above the catalyst layer(s) in the reaction tube(s) or above a tube-holding upper plate in the reactor.

As examples of gas-phase catalytic oxidation to be conducted according to this invention, one for producing unsaturated aldehyde and/or unsaturated carboxylic acid from unsaturated hydrocarbon and the like; one for producing unsaturated carboxylic acid from unsaturated aldehyde; one for producing unsaturated nitrile from unsaturated hydrocarbon and ammonia; and one for producing unsaturated carboxylic acid from saturated hydrocarbon can be named.

Of these gas-phase catalytic oxidation operations, the present invention is favorably used in the gas-phase catalytic oxidation for producing unsaturated carboxylic acid from unsaturated hydrocarbon and the like, via unsaturated aldehyde, in particular, in that for producing acrylic acid from propylene via acrolein. For example, in such acrylic acid production from propylene via acrolein, the present invention is effective, in respect of propylene-oxidizing catalyst ("the first stage catalyst"), for suppressing its deterioration caused by the catalyst inhibitor originating from impurities contained in the starting propylene or, when the reaction gas is recycled, its deterioration caused by the catalyst inhibitor contained in the recycled gas. It is also effective, in respect of acrolein-oxidizing catalyst ("the second stage catalyst"), to suppress the detrimental influence on the second stage catalyst of the by-products formed in the first stage reaction. Furthermore, the invention is also effective in production of acrylic acid using propane as the starting material.

The catalyst to be used in such gas-phase catalytic oxidation is not particularly limited, so long as it is one generally used in this kind of reaction. Specifically, for example, as the catalyst for the first stage gas-phase catalytic oxidation for producing acrolein from propylene, such complex oxide catalyst as expressed by the following formula (1):

$$Mo_aW_bBi_cFe_dA_eB_fC_gD_hO_x \qquad (1)$$

[in which Mo is molybdenum; W is tungsten; Bi is bismuth; Fe is iron; A is at least one element selected from nickel and cobalt; B is at least an element selected from alkali metals, alkaline earth metals and thallium; C is at least an element selected from phosphorus, arsenic, boron and niobium; D is at least an element selected from silicon, aluminum and titanium; and O is oxygen; and a, b, c, d, e, f, g, h and x stand for the atomic ratios of Mo, W, Bi, Fe, A, B, C, D and O, respectively, satisfying the inequalities, where $2 \leq a \leq 10$, $0 \leq b \leq 10$ and $a+b=12$, $0.1 \leq c \leq 10$, $0.1 \leq d \leq 10$, $1 \leq e \leq 20$, $0.005 \leq f \leq 3$, $0 \leq g \leq 4$, and $0 \leq h \leq 15$, respectively, x being a numeral value determined according to the state of oxidation of each of the elements] are preferred.

Also as the catalyst for the second stage gas-phase catalytic oxidation for producing acrylic acid from acrolein, such complex oxide catalyst as expressed by the following formula (2):

$$Mo_mV_nQ_qR_rS_sT_tO_y \qquad (2)$$

[in which Mo is molybdenum; V is vanadium; Q is at least an element selected from tungsten and niobium; R is at least an element selected from iron, copper, bismuth, chromium and antimony; S is at least an element selected from alkali metals and alkaline earth metals; T is at least an element selected from silicon, aluminum and titanium; and O is oxygen; and m, n, q, r, s, t and y stand for the atomic ratios of Mo, V, Q, R, S, T and O, respectively, satisfying the inequalities, where m=12, $2 \leq n \leq 14$, $0 \leq q \leq 12$, $0 \leq r \leq 6$, $0 \leq s \leq 6$, $0 \leq t \leq 30$, respectively, x being a numeral value determined according to the state of oxidation of each of the elements] are particularly preferred.

In the production method of the present invention, acrylic acid which is a final product is produced by the gas-phase catalytic oxidation of propylene as a starting material with molecular oxygen for producing mainly acrolein as an intermediate compound, and the following gas-phase catalytic oxidation of the acrolein with molecular oxygen. In that occasion, preferably a fixed bed reactor having a reaction tube(s) filled with a first stage catalyst for producing acrolein by gas-phase catalytic oxidation of propylene with molecular oxygen and a reaction tube(s) filled with a second stage catalyst for producing acrylic acid by gas-phase catalytic oxidation of the acrolein is used. In this fixed bed reactor, the treating agent can be disposed, in respect of the direction of the gas flow, on the upstream side of the first stage catalyst or the second stage catalyst.

As reaction conditions for the gas-phase catalytic oxidation, they may be substantially the same to those commonly used in gas-phase catalytic oxidation in general, except that the treating agent is disposed in the reactor, and are not particularly limited. For example, in the production of acrolein or acrylic acid by gas-phase catalytic oxidation of propylene or propane, a gaseous mixture of 1-15 volume %, preferably 4-12 volume %, of a starting compound such as propylene or propane; 1-10 volume times, preferably 1.5-8 volume times, the starting compound of molecular oxygen; and an inert gas (e.g., nitrogen, carbon dioxide, steam or the like) as the diluent; is contacted with the catalyst at a temperature within a range of 250°-450° C., preferably 260°-400° C., under a pressure within a range of atmospheric pressure-1 MPa, preferably not higher than 0.8 MPa, and at a space velocity (STP) within a range of 300 $h^{-1}$-5000 $h^{-1}$, preferably 500 $h^{-1}$-4000 $h^{-1}$ to effect the reaction.

According to the invention, as demonstrated by the following Examples, the gas-phase catalytic oxidation can be carried out free of catalyst deterioration, maintaining a high yield level and suppressing increase in pressure loss, whereby making stable continuous operations over a prolonged period possible. Therefore, according to the production method of the present invention, acrolein or acrylic acid can be obtained at high yield efficiently with stability.

EXAMPLES

Hereinafter the present invention is explained more specifically, referring to working Examples, it being understood that the invention of course is in no way limited by the Examples, but can be practiced with any suitable modifications to the extent meeting the spirit of the foregoing and following descriptions. All of such modifications are included within the technical scope of the present invention.

<Catalytic Performance>

The performance was evaluated by the acrylic acid yield as defined by the following equation:

Acrylic acid yield(mol %) =(mol number of formed acrylic acid/mol number of fed propylene)×100.

<Preparation of Gas-Phase Oxidation Catalyst I>

The gas-phase oxidation catalysts which were used in the experiments, i.e., the first stage catalyst used for gas-phase catalytic oxidation of propylene with molecular oxygen for producing acrolein, and the second stage catalyst used for gas-phase catalytic oxidation of acrolein with molecular oxygen for producing acrylic acid, were prepared following the method as described in Example 1 of JP Sho 64(1989)-63543A.

The composition of these catalysts excluding the carriers and oxygen were as follows, in terms of the atomic ratios:

first stage catalyst;

$Co_4Fe_1Bi_1W_2Mo_{10}Si_{1.35}K_{0.06}$ second stage catalyst;

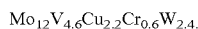
$Mo_{12}V_{4.6}Cu_{2.2}Cr_{0.6}W_{2.4}.$

<Measurement of Pressure Loss at the Catalyst Layer>

In the present invention, the pressure loss was measured as follows: leaving the lower part of the reaction tube open, the pressure under passing air at a rate of 30 L (liter)/min (standard state) from the upper part of the reaction tube was measured, and the difference from the initial pressure was determined.

Example 1

First, 75 mass parts of alumina powder of 5 µm in average particle size and 5 mass parts of methyl cellulose as a binder were thrown into a kneader and mixed thoroughly. Then 8 mass parts of alumina sol as $Al_2O_3$ of 10 nm in average particle size and 17 mass parts of colloidal silica as $SiO_2$ of 10 nm in average particle size were added to the mixture, further an adequate amount of water was added and mixed. The mixture was extrusion molded, dried and calcined for 2 hours at 1000° C., to provide a columnar alumina-silica treating agent (A) of, on the average, 7 mm in outer diameter and 7 mm in length.

Two steel reaction tubes of each 25 mm in inner diameter and 3000 mm in length and equipped with an outer jacket for circulating a heat transfer medium were put ready, one of which was filled with the first stage catalyst to a length of 2450 mm, interposed from the bottom by 500 mm of empty space (the first reaction tube). The other reaction tube was filled with the second stage catalyst and the treating agent (A). The second stage catalyst occupied 2000 mm of the tube from the bottom and the treating agent (A) occupied 500 mm on the second stage catalyst (the second reaction tube). The upper ends of the two reaction tubes were connected with a steel pipe of 20 mm in inner diameter and 4000 mm in length, which could be externally heated with an electric heater.

Then a gaseous mixture of 5 volume % of propylene, 10 volume % of oxygen, 25 volume % of steam and 60 volume % of nitrogen was introduced into the first reaction tube from its lower end as the starting gas, at a space velocity to the first stage catalyst of 2200 $h^{-1}$ (STP) to conduct the gas-phase catalytic oxidation. In that occasion, the reaction temperature (temperature of the heat transfer medium) in the first reaction tube was 325° C., the reaction temperature (temperature of the heat transfer medium) in the second reaction tube was 260° C., and the connecting pipe was kept at 170° C.

While exchanging the treating agent (A) once in every 4000 hours, the gas-phase catalytic oxidation of propylene using the above reaction apparatus was continuously run for 9600 hours. At the end of the 4000 hours', 8000 hours' and 9600 hours' operation, the outlet gas from the second reaction tube was analyzed, and the pressure loss at the second stage catalyst layer after extracting the treating agent (A) was measured. At the time points where 4000 hours and 8000 hours had passed, new treating agent (A) was filled again after the measurement of the pressure loss at the second stage catalyst layer, and the reaction was continued.

As a result, no increase in the pressure loss at the second stage catalyst layer compared with that in the incipient period of the reaction was observed. The acrylic acid yields before each extraction of the treating agent (A) were 88.7 mol %, 87.2 mol % and 86.6 mol %, respectively.

Example 2

Gas-phase catalytic oxidation reaction of propylene was operated in the same manner as Example 1, except that the treating agent was exchanged only once after 8000 hours had passed. After the 8000 hours' reaction, the treating agent was extracted and the pressure loss at the catalyst layer was measured. The increase in the pressure loss compared with that in the incipient period was 0.1 kPa. Also the acrylic acid yield at the time was 85.6 mol %.

Example 3

Gas-phase catalytic oxidation of propylene was operated continuously for 9600 hours in the same manner as Example 1, except that the treating agent was not exchanged. After the 9600 hours had passed, the treating agent was extracted and the pressure loss at the catalyst layer was measured. The increase in the pressure loss compared with that in the incipient period was 2.1 kPa. Also the acrylic acid yield at that time was 82.7 mol %.

Examples 4-7

Example 1 was repeated except that the treating agent which was prepared by replacing the colloidal silica with magnesium carbonate (Example 4), calcium carbonate (Example 5) or zirconium oxide (Example 6), respectively, or by replacing the alumina with titanium oxide (Example 7) was used in each run.

As the result, in none of the cases any increase in pressure loss at the second stage catalyst layer was observed.

Example 8

Gas-phase catalytic oxidation of propylene was operated continuously for 4000 hours in the same manner as Example 1.

Thereafter the treating agent (A) was extracted, and the used treating agent (A) was regenerated by a calcination at 500° C. for 5 hours in an atmosphere of air. Thus regenerated treating agent (A) was refilled and the gas-phase catalytic oxidation reaction of propylene was continued. Thereafter reaction was operated for 4000 hours and the pressure loss at the second stage catalyst layer was measured in the manner similar to Example 1. No increase in the pressure loss over that at the initial stage of the reaction was observed.

<Preparation of Gas-Phase Oxidation Catalyst II>

A first stage catalyst to be used for producing acrolein by gas-phase catalytic oxidation of propylene with molecular oxygen, and a second stage catalyst to be used for producing acrylic acid by gas-phase catalytic oxidation of acrolein with molecular oxygen were prepared, following the method as described in Example 1 of JP Sho 64(1989)-63543A. The composition of these catalysts excluding the carriers and oxygen were as follows, in terms of the atomic ratio:

first stage catalyst;

$Co_4Fe_{1.1}Bi_{1.1}W_1Mo_{10}Si_1K_{0.07}$ second stage catalyst;

$Mo_{12}V_5Cu_2Cr_{0.5}W_2.$

<Preparation of Treating Agents>

Treating Agent (A)

Seventy (70) mass parts of alumina powder of 15 μm in average particle diameter and 5 mass parts of starch as the binder were thrown into a kneader and thoroughly mixed. Then 30 mass parts of colloidal silica as $SiO_2$ of 50 nm in average particle size was added, and further an adequate amount of water was added, followed by mixing. This mixture was extrusion molded, dried and calcined for 2 hours at 800° C., to provide a columnar alumina-silica treating agent (A) of, on the average, 7 mm in outer diameter and 7 mm in length.

Treating agents (B)-(D)

Preparation steps of the treating agent (A) were repeated except that the colloidal silica was replaced by titania sol [treating agent (B)] or zirconia sol [treating agent (C)], or the alumina was replaced with titanium oxide [treating agent (D)], to provide treating agents (B), (C) and (D), respectively.

Treating Agent (E)

Treating agent (E) was prepared in the manner similar to treating agent (A), except that the amount of the alumina powder was increased to 90 mass parts, that of the colloidal silica as $SiO_2$ was changed to 10 mass parts and the calcining temperature was raised to 1000° C.

Treating Agents (A2) and (A3)

Treating agents (A2) and (A3) were prepared in the manner similar to treating agent (A), except that their dimensions were made 9 mm in outer diameter ×9 mm in length [treating agent (A2)] and 5 mm in outer diameter ×5 mm in length [treating agent (A3)], respectively.

<Measurement of Adsorption Capacity of Organic Substance>

Fifty (50) g of a treating agent was weighed, filled in the fixed bed flowing apparatus and maintained at 350° C. Nitrogen gas after bubbling in crotonaldehyde maintained at 10° C. was introduced thereinto from the upstream side of the treating agent at a rate of 170 ml/min. for an hour. After the adsorption treatment, the whole amount of the treating agent was heat-treated in air up to 500° C., and the mass change before and after the heat treatment was measured.

The adsorption capacity of organic substance was determined by the following equation:

adsorption capacity of organic substance(mass %) = [weight reduction(g)/treating agent(g)]×100

Example 9

Two steel reaction tubes of each 25 mm in inner diameter and 3000 mm in length, which were equipped with an outer jacket for circulating a heat transfer medium were put ready, one of which (the first reaction tube) was filled with the first stage catalyst from the reaction gas inlet side (upper end) to a length of 2450 mm, leaving a space of 300 mm thereabove. The other reaction tube (the second reaction tube) was filled with the treating agent (A) and the second stage catalyst, respectively to the length of 500 mm and 2200 mm from the reaction gas inlet side (upper end). The outlet (lower end) of the first reaction tube and the inlet (upper end) of the second reaction tube were connected with a steel pipe of 20 mm in inner diameter and 4000 mm in length, which could be externally heated with an electric heater.

Then a gaseous mixture of 5 volume % of propylene, 10 volume % of oxygen, 15 volume % of steam and 70 volume % of nitrogen was introduced as the starting gas into the first reaction tube from the inlet side, at a space velocity to the first stage catalyst of 1200 h$^{-1}$ (STP) to carry out the gas-phase catalytic oxidation. In that occasion, the reaction temperature (temperature of the heat transfer medium) in the first reaction tube was 325° C., and the reaction temperature (temperature of the heat transfer medium) in the second reaction tube was 260° C., and the connecting pipe was kept at 170° C.

While exchanging the treating agent (A) once in every 4000 hours, the gas-phase catalytic oxidation of propylene using the above reaction apparatus was continuously operated for 9600 hours. At the end of the 4000 hours', 8000 hours' and 9600 hours' operation, the gas leaving the outlet (lower end) of the second reaction tube was analyzed and the pressure loss at the second stage catalyst layer was measured after extracting the treating agent (A). Thereafter new treating agent (A) was filled again and the reaction was continued. The acrylic acid yields and the variation in pressure loss at the second stage catalyst layer were as shown in Table 1.

Example 10

Gas-phase catalytic oxidation of propylene was continuously operated in the same manner as Example 9, except that the treating agent was changed only once after 8000 hours' operation. The acrylic acid yields and the variation in pressure loss at the second stage catalyst layer were as shown in Table 1.

Example 11

Gas-phase catalytic oxidation of propylene was operated in the same manner as Example 9, except that ceramic balls whose adsorption capacity measured by crotonaldehyde as an indicator of organic substance was 0.01 mass % was used in place of treating agent (A). The reaction was operated continuously for 9600 hours, while exchanging the ceramic balls after 4000 hours' and 8000 hours' operation. The acrylic acid yields and the variation in pressure loss at the second stage catalyst layer were as shown in Table 1.

Example 12

Gas-phase catalytic oxidation of propylene was operated in the same manner as Example 11, except that the ceramic balls were exchanged only once after 8000 hours' operation. The acrylic acid yields and the variation in pressure loss at the second stage catalyst layer were as shown in Table 1.

Examples 13-16

Example 9 was repeated, except that the treating agent was replaced with treating agent (B) (Example 13), treating agent (C) (Example 14), treating agent (D) (Example 15) or treating agent (E) (Example 16), respectively. These adsorption capacities of each treating agents measured by crotonaldehyde as an indicator of organic substance, acrylic acid yields and the variation in pressure loss at the second stage catalyst layer were as shown in Table 1.

Example 17

Gas-phase catalytic oxidation of propylene was operated continuously for 4000 hours in the same manner as Example 9. Thereafter treating agent (A) was extracted, and the used treating agent (A) was regenerated by 5 hours' calcination treatment at 500° C. in an atmosphere of air. Thus regenerated treating agent (A) was refilled and the reaction was continued. The acrylic acid yields and the pressure losses at the second stage catalyst layer in this run were as shown in Table 1.

Example 18

Gas-phase catalytic oxidation of propylene was operated continuously in the same manner as Example 9, except that the treating agent (A) occupying 500 mm of the second reaction tube was replaced with a packed layer formed of two kinds of treating agents, i.e., 250 mm of the treating agent (A2) at the upstream side and 250 mm of the treating agent (A3) at the downstream side. The acrylic acid yields and the pressure losses at the second stage catalyst layer were as shown in Table 1.

Example 19

Gas-phase catalytic oxidation of propylene was operated in the same manner as Example 9, except that the empty space in the first reaction tube was filled with treating agent (A), to a length of 200 mm. An acrylic acid collector was connected at the outlet of the second reaction tube, to catch the acrylic acid. The acrylic acid collection was 95%. Fifty (50) % of the exit gas leaving the collector, including steam, was recycled into the inlet of the first reaction tube. Propylene and air were added to the recycled gas to so adjust the latter's concentration that it contained 5 volume % of propylene, 10 volume % of oxygen and 15 volume % of steam. All other operating conditions were same manner as Example 9. The acrylic acid yields and the variation in pressure loss at the first stage catalyst layer were as shown in Table 1.

TABLE 1

|  | Treating Agent | Adsorption Capacity of Crotonaldehyde (mass %) | Acrylic Acid Yield and Pressure Loss at the Second Stage | | After 4000 hrs. | After 8000 hrs. | After 9600 hrs. |
|---|---|---|---|---|---|---|---|
| Example 9 | (A) | 0.28 | Acrylic acid yield (%) | | 87.7 | 86.2 | 85.9 |
|  |  |  | Pressure loss at the second stage (KPa) | Before extraction of treating agent | 3.1 | 3.1 | 2.9 |
|  |  |  |  | After extraction of treating agent | 2.8 | 2.8 | 2.8 |
| Example 10 | (A) | 0.28 | Acrylic acid yield (%) | | 87.6 | 85.6 | 84.9 |
|  |  |  | Pressure loss at the second stage (KPa) | Before extraction of treating agent | — | 4.4 | 3.0 |
|  |  |  |  | After extraction of treating agent | — | 2.9 | 2.9 |
| Example 11 | ceramic balls | 0.01 | Acrylic acid yield (%) | | 86.7 | 85.3 | 84.4 |
|  |  |  | Pressure loss at the second stage (KPa) | Before extraction of treating agent | 3.6 | 4.6 | 5.3 |
|  |  |  |  | After extraction of treating agent | 3.3 | 4.4 | 5.2 |
| Example 12 | ceramic balls | 0.01 | Acrylic acid yield (%) | | 86.7 | 83.7 | 83.0 |
|  |  |  | Pressure loss at the second stage (KPa) | Before extraction of treating agent | — | 4.8 | 5.4 |
|  |  |  |  | After extraction of treating agent | — | 4.6 | 5.2 |
| Example 13 | (B) | 0.22 | Acrylic acid yield (%) | | 87.6 | 86.1 | 85.8 |
|  |  |  | Pressure loss at the second stage (KPa) | Before extraction of treating agent | 3.2 | 3.2 | 3.0 |
|  |  |  |  | After extraction of treating agent | 2.8 | 2.8 | 2.8 |

TABLE 1-continued

| | Treating Agent | Adsorption Capacity of Crotonaldehyde (mass %) | Acrylic Acid Yield and Pressure Loss at the Second Stage | | After 4000 hrs. | After 8000 hrs. | After 9600 hrs. |
|---|---|---|---|---|---|---|---|
| Example 14 | (C) | 0.18 | Acrylic acid yield (%) | | 87.5 | 86 | 85.2 |
| | | | Pressure loss at the second stage (KPa) | Before extraction of treating agent | 3.2 | 3.2 | 3.0 |
| | | | | After extraction of treating agent | 2.8 | 2.8 | 2.8 |
| Example 15 | (D) | 0.33 | Acrylic acid yield (%) | | 87.8 | 86.4 | 86.0 |
| | | | Pressure loss at the second stage (KPa) | Before extraction of treating agent | 3.2 | 3.2 | 3.0 |
| | | | | After extraction of treating agent | 2.8 | 2.8 | 2.8 |
| Example 16 | (E) | 0.05 | Acrylic acid yield (%) | | 87.2 | 85.7 | 85.1 |
| | | | Pressure loss at the second stage (KPa) | Before extraction of treating agent | 3.3 | 3.3 | 3.0 |
| | | | | After extraction of treating agent | 2.8 | 2.9 | 2.9 |
| Example 17 | (A) regenerated | 0.28 | Acrylic acid yield (%) | | 87.6 | 86.3 | 85.8 |
| | | | Pressure loss at the second stage (KPa) | Before extraction of treating agent | 3.1 | 3.1 | 2.9 |
| | | | | After extraction of treating agent | 2.8 | 2.8 | 2.8 |
| Example 18 | (A2) (A3) laminated | 0.28 | Acrylic acid yield (%) | | 87.7 | 86.2 | 85.7 |
| | | | Pressure loss at the second stage (KPa) | Before extraction of treating agent | 3.1 | 3.1 | 2.9 |
| | | | | After extraction of treating agent | 2.8 | 2.8 | 2.8 |
| Example 19 | (A) | 0.28 | Acrylic acid yield (%) | | 87.9 | 86.5 | 86.1 |
| | | | Pressure loss at the second stage (KPa) | Before extraction of treating agent | 3.2 | 3.2 | 3.1 |
| | | | | After extraction of treating agent | 3.1 | 3.1 | 3.1 |

INDUSTRIAL UTILIZABILITY

In the gas-phase catalytic oxidation according to the present invention, catalyst deterioration is remarkably suppressed, while maintaining a high yield level and inhibiting increase in pressure loss, thus enabling stable continuous operation over a prolonged period. Besides, there is no necessity to exchange costly catalyst. Therefore, according to the method of the present invention, production cost of fundamental chemicals such as acrylic acid obtainable by gas-phase catalytic oxidation can be markedly reduced.

Comparative Example 1

Gas-phase catalytic oxidation reaction of propylene was operated in the same manner as Example 9, for 8000 hours continuously, except that no treating agent was used. The acrylic acid yield and the pressure loss at the second stage catalyst layer were as shown in Table 2.

The drop in the acrylic acid yield and rise in the pressure loss were very substantial and continuation of further reaction was given up.

TABLE 2

| | Treating Agent | Adsorption Capacity of Crotonaldehyde (mass %) | Acrylic Acid Yield and Pressure Loss at the Second Stage | After 8000 hrs. |
|---|---|---|---|---|
| Comparative Example 1 | None | — | Acrylic acid yield (%) | 82.4 |
| | | | Pressure loss at the second stage (KPa) | 6.4 |

The invention claimed is:

1. A method for gas-phase catalytic oxidation in a fixed bed reactor including a gas-phase oxidation catalyst layer, wherein a treating agent for removing organic substance and/or carbides is disposed on the upstream side of the gas-phase oxidation catalyst layer in respect of the direction of the gas flow, the adsorption capacity of the treating agent being at least 0.05% by mass, as measured by crotonaldehyde as an indicator of organic substance, in which the gas phase catalytic oxidation reaction is that for producing (meth)acrylic acid through two-stage reaction of propylene, isobutylene, t-butyl alcohol or methyl-t-butyl ether, including a catalyst for the first stage reaction and a catalyst for the second stage reaction, and wherein said treating agent is selected from the group consisting of silica-alumina, silica-titania, silica-zinc oxide, silica-zirconia, alumina-titania, alumina-zinc oxide, alumina-zirconia, titania-zirconia, zinc oxide-zirconia, zeolite, magnesium carbonate and calcium carbonate.

2. The method according to claim 1, in which the treating agent is disposed in a reaction tube or tubes and/or in a space within the reactor, at a position on the upstream side of the catalyst layer in respect of the direction of the gas flow.

3. The method according to claim 1, in which at least a part of the treating agent is exchanged at a frequency of at least once a year.

4. The method according to claim 1, in which at least a part of the treating agent is that which has been regenerated.

5. A process for producing (meth)acrylic acid according to claim 1, which uses a fixed bed reactor wherein the treating agent is disposed on the downstream side of the catalyst for the first stage reaction and on the upstream side of the catalyst for the second stage reaction, in respect of the direction of the gas flow.

* * * * *